(12) United States Patent
Ryder

(10) Patent No.: US 7,578,300 B2
(45) Date of Patent: Aug. 25, 2009

(54) MOTORIZED FOOT SANDER

(76) Inventor: Jeff G. Ryder, 1994 Manning Court, Kamloops, BC (CA) V2E 2R8

( * ) Notice: Subject to any disclaimer, the term of this patent is extended or adjusted under 35 U.S.C. 154(b) by 461 days.

(21) Appl. No.: 11/418,284

(22) Filed: May 4, 2006

(65) Prior Publication Data

US 2007/0256698 A1 Nov. 8, 2007

(51) Int. Cl.
*A45D 29/05* (2006.01)
(52) U.S. Cl. .................... 132/73.6; 132/75.8
(58) Field of Classification Search ............ 132/75.8, 132/73.6, 73.5, 73; 451/357, 359
See application file for complete search history.

(56) References Cited

U.S. PATENT DOCUMENTS

| 3,733,634 | A | * | 5/1973 | Golbe | 15/28 |
| 4,328,819 | A | * | 5/1982 | Haas | 132/73.6 |
| 5,419,737 | A | * | 5/1995 | Brazell et al. | 451/453 |
| 6,190,245 | B1 | * | 2/2001 | Heidelberger et al. | 451/357 |
| 7,377,282 | B2 | * | 5/2008 | O'Dwyer | 132/73.6 |

* cited by examiner

*Primary Examiner*—Robyn Doan

(57) ABSTRACT

An abrading and smoothing tool includes a handle element that is adapted to be easily grasped by the user and comfortably held in the palm of the hand, and which contains a small electrically-powered multi-speed motor. A segment of abrasive material, such as sandpaper, is removably attached to the hand held portion of the device by hook-and-loop fastener means to be easily removed from the device after use so that the abrasive material can be quickly and easily replaced.

2 Claims, 1 Drawing Sheet

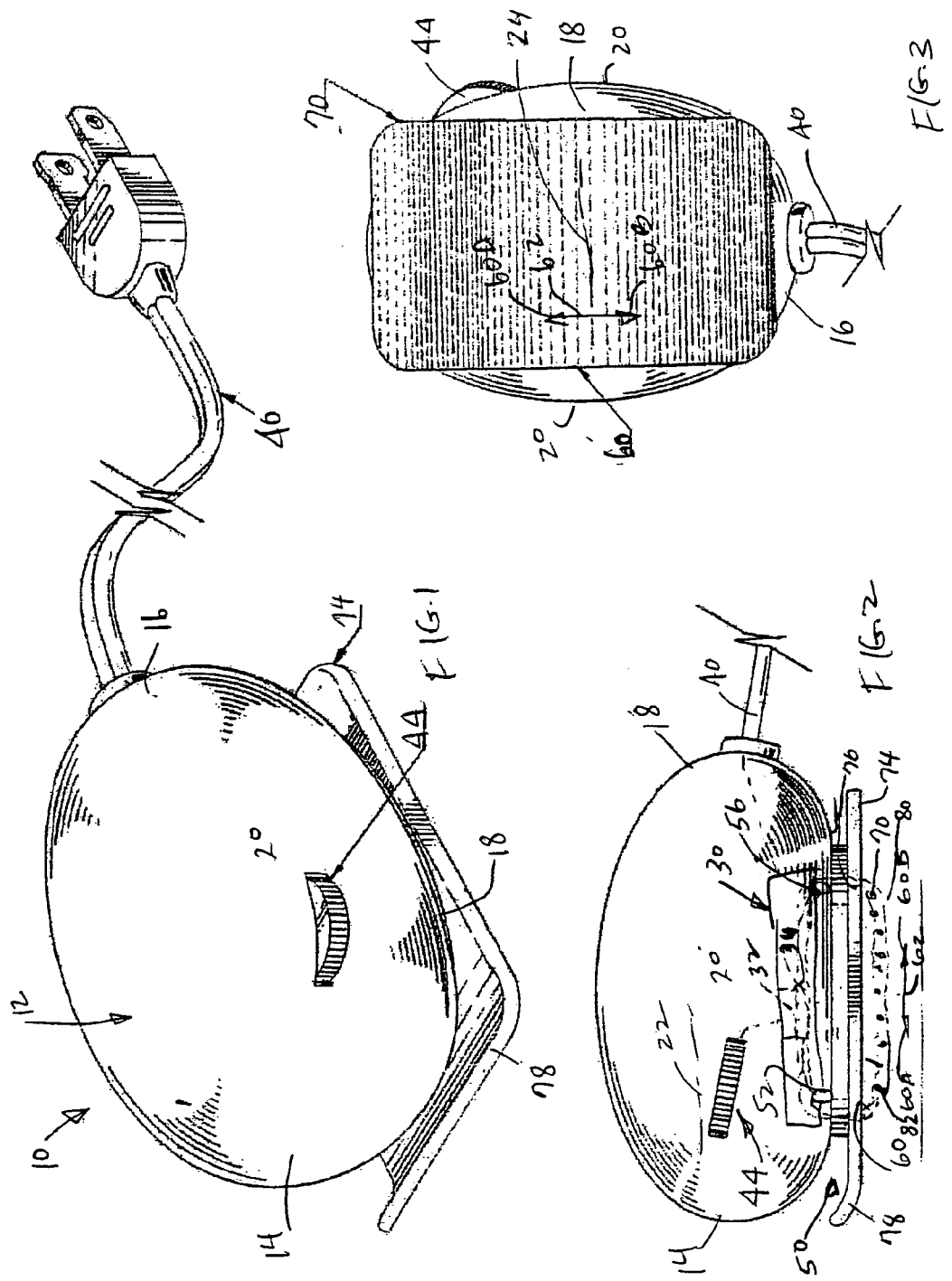

MOTORIZED FOOT SANDER

TECHNICAL FIELD OF THE INVENTION

The present invention relates in general to toiletries and in particular to a tool for abrading and/or smoothing skin.

BACKGROUND OF THE INVENTION

For health, cosmetic and economic reasons it frequently becomes desirable or necessary to abrade or smooth skin. Health and cosmetic reasons include, among others, the reduction or smoothing of calluses, growths and irregular skin areas, the removal of dead skin and skin stimulation. Economic reasons include health cost savings and any economic value of cosmetic improvements, and may also include non-health expense reduction and convenience, for example benefits derived from smoothing of women's feet that become rough resulting in less snagged and ruined nylon stockings.

While skin creams may be of some benefit, the inventor has discovered that creams which are available to the general public are not adequate to fully abrade or smooth skin in all cases. Therefore, there is a need for a means for smoothing or abrading skin which is effective and which is available to the general public.

Heretofore, abrading or smoothing has usually involved action by an individual or by a professional acting upon an individual, scraping or paring the skin with a sharp knife or knife-like instrument or abrading the skin with sandpaper, emery cloth, pumice stone or a metal file. The use of any sharp instrument is tedious and dangerous, particularly for the unskilled or less than dextrous, as care must be exercised to avoid cutting too deep and causing injury to underlying tissue. Metal files are not generally acceptable for such use, not being designed for such use, being cumbersome and often being unpleasant to the touch, seeming cold.

The use of sandpaper or emery cloth has been effective, but not as effective as possible because these devices still require dexterity and the ability to reach the area of interest on the body. This may be difficult for those with disabilities or those who cannot easily reach their feet. Sandpaper or emery cloth material is usually wrapped around the ends of the user's fingers or around some other shaped item and then reciprocated or rotated over the area to be abraded or smoothed. Hand holding the material in place during use has been difficult and tiresome. Even if held by a device, sandpaper tends to crack and fray and the abrasive particles may separate from the backing material. Sandpaper and emery cloth must also be replaced frequently because of cracking and fraying and because the abrasive-surface voids become filled with abraded skin fragments. This may also result in an undesirable interruption of the abrading process.

Pumice stone has been more commonly used for such abrading or smoothing. However, such pumice stone becomes smooth, losing abrasive quality with use as the voids in the abrasive surface become filled with abraded skin fragments. This requires periodic brushing or flushing with air or liquid to maintain the abrasive capability of the stone. Further pumice stones are fragile and often break with such use.

In the case of cutting instruments or in the case of individuals who cannot easily reach the area to be treated, a professional must be employed. This may be too expensive for some people who otherwise require the treatment.

In addition, the prior known techniques do not lend themselves well to use by handicapped or older people whose manual dexterity is reduced or impaired.

Still further, it is sometimes difficult to change the abrading portion of those devices known to the inventor. This difficulty adds to the already annoying process.

SUMMARY OF THE INVENTION

The disadvantages of the prior known techniques are overcome in the present invention by provision of an abrading and smoothing tool which includes a handle element that is adapted to be easily grasped by the user and comfortably held in the palm of the hand, and which contains a small electrically-powered multi-speed motor. A segment of abrasive material, such as sandpaper, is removably attached to the hand held portion of the device by hook-and-loop fastener means to be easily removed from the device after use so that the abrasive material can be quickly and easily replaced.

The device embodying the present invention provides an abrading or smoothing tool for skin which is easy for an unskilled person to handle and control, is comfortable to work with, and is useable at a variety of angles to accommodate abrading or smoothing of various body contours while being durable and abrades or smooths rapidly. The device can be easily and quickly cleaned, washed or sanitized and is easily assembled/disassembled tool which has an easily replaceable abrasive surface.

Other systems, methods, features, and advantages of the invention will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWING FIGURES

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is a perspective view of a skin smoothing and abrading device embodying the present invention.

FIG. 2 is a side elevational view of the device embodying the present invention.

FIG. 3 is a bottom view of the device shown in FIG. 1.

DETAILED DESCRIPTION OF THE INVENTION

Referring to the figures, it can be understood that the present invention is embodied in a skin smoothing and abrading device 10. Device 10 comprises an egg-shaped hollow housing 12. The egg shape of the housing making that housing very comfortable to hold and easy to use. The housing has a first portion 14 that is a forward portion when the housing is in use, a second portion 16 that is an aft portion when the housing is in use, a third portion 18 that is a bottom portion when the housing is in use and a fourth portion 20 that is a side portion when the housing is in use. A longitudinal axis 22 extends between first portion 14 and second portion 16 and a transverse axis 24 extends transverse to the longitudinal axis.

A motor unit 30 is located in the housing. Motor unit 30 has a speed control circuit 32 and an output drive element 34. The speed control circuit and the details of the connection between the motor and the output drive element are well known to those skilled in the motor art. These details are not important to the present invention and will not be claimed. As such, the details of the motor, its circuits and elements and the output drive will not be disclosed.

A power cord 40 is attached to the motor unit and extends through the second portion of the housing. A motor speed control knob 44 is located on fourth portion 20 of the housing. The motor speed control knob also acts as the on/off switch for the motor. An abrading element mounting unit 50 is located on third portion 18 of the housing. Abrading element mounting unit 50 includes a first rotor element 52 mounted on output drive element 34 of the motor unit to be moved by the output drive element when the motor unit is activated. First rotor element 52 is located adjacent to first portion 14 of the housing and extends in the direction of the transverse axis of the housing.

A second rotor element 56 is located adjacent to second portion 16 of the housing and extends in the direction of the transverse axis of the housing. The rotor elements rotate in the direction of the longitudinal axis from the front of the housing toward the rear of the housing or vice versa.

An abrading element mounting element 60 is mounted on the first and second rotor elements for movement therewith in the directions 60A or 60B as indicated by the double-headed arrow 62 in FIGS. 2 and 3. The abrading element thus rotates on the housing in the direction of the longitudinal axis of the housing from front to rear of the housing in direction 60A or direction 60B.

Hook-and-loop fastener elements 70 are mounted on the abrading element mounting element. A guide plate 74 is mounted on the housing adjacent to the abrading element mounting element and has an opening 76 defined therethrough. The abrading element mounting element extends through the opening in the guide plate. The guide plate further includes a curved portion 78 which is located adjacent to first portion 14 of the housing. The curved portion of the guide plate smooths the skin of the user during use of device 10.

An abrading element 80, such as sandpaper suitable for use on skin or the like, has hook-and-loop fastener elements 82 thereon. Abrading element 80 is releasably mounted on the housing via interconnection of hook-and-loop fastener elements 82 on the abrading element and hook-and-loop fastener elements 70 on abrading element mounting element 60.

Use of device 10 can be understood from the teaching of the foregoing disclosure and as such will be only briefly discussed. A user simply places an abrading element, such as sandpaper or the like, on the abrading element mounting element using the hook-and-loop fasteners, then operates the on/off/speed control knob to activate the motor and to select the desired operating speed. Then user then simply places the device so the abrading element contacts the desired portion of the user and abrades that portion. Once the abrading operation is completed, after shutting off the motor, the user can remove the abrading element from the housing since the hook-and-loop fasteners are easily separated and can then discard the used abrading element.

While various embodiments of the invention have been described, it will be apparent to those of ordinary skill in the art that many more embodiments and implementations are possible within the scope of this invention. Accordingly, the invention is not to be restricted except in light of the attached claims and their equivalents.

What is claimed is:

1. A skin smoothing and abrading device comprising:
A) an egg-shaped housing having
  (1) a first portion that is a forward portion when the housing is in use,
  (2) a second portion that is an aft portion when the housing is in use,
  (3) a third portion that is a bottom portion when the housing is in use,
  (4) a fourth portion that is a side portion when the housing is in use,
  (5) a longitudinal axis which extends between the first portion and the second portion, and
  (6) a transverse axis which extends transverse to the longitudinal axis;
B) a motor unit in the housing, the motor unit having
  (1) a speed control circuit, and
  (2) an output drive element;
C) a power cord attached to the motor unit and extending through the second portion of the housing;
D) a motor speed control knob on the fourth portion of the housing;
E) an abrading element mounting unit on the third portion of the housing and including
  (1) a rotor element mounted on the output drive element of the motor unit to be moved by the output drive element when the motor unit is activated, the rotor element extending in the direction of the transverse axis of the housing,
  (2) an abrading element mounting element mounted on the rotor element for movement therewith,
  (3) a hook-and-loop fastener element mounted on the abrading element mounting element, and
  (4) a guide plate mounted on the housing adjacent to the abrading element mounting element and having an opening defined therethrough;
F) an abrading element having a hook-and-loop fastener element thereon, the abrading element being releasably mounted on the housing via interconnection of the hook-and-loop fastener element on the abrading element and the hook-and-loop fastener element on the abrading element mounting element; and
G) a second rotor element located adjacent to the second portion of the housing and wherein the abrading element of the abrading element mounting unit is trained around the rotor elements for movement therewith.

2. A skin smoothing and abrading device comprising:
A) a hollow egg-shaped housing having a forward portion and aft portion;
B) a motor unit in the housing;
C) an abrading element mounting unit on the housing and including
  (1) an abrading element mounting element connected to the motor element for rotation,
  (2) a hook-and-loop fastener element mounted on the abrading element mounting element,
  (3) a guide plate mounted on the housing adjacent to the abrading element mounting element and having an opening defined therethrough, and
  (4) a rotor element mounted on the output drive element of the motor unit to be moved by the output drive element when the motor unit is activated;
D) an abrading element having a hook-and-loop fastener element thereon, the abrading element being releasably mounted on the housing via interconnection of the hook-and-loop fastener element on the abrading element and the hook-and-loop fastener element on the abrading element mounting element; and
E) a second rotor element located adjacent to the aft portion of the housing and wherein the abrading element of the abrading element mounting unit is trained around the rotor elements for movement therewith.

* * * * *